US00PP18090P3

(12) United States Plant Patent

Lintott

(10) Patent No.: US PP18,090 P3
(45) Date of Patent: Sep. 25, 2007

(54) *CHRYSANTHEMUM* PLANT NAMED 'POSH PINK'

(50) Latin Name: *Chrysanthemum morifolium*
Varietal Denomination: Posh Pink

(75) Inventor: Keith G. Lintott, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 11/396,884

(22) Filed: Apr. 3, 2006

(65) Prior Publication Data

US 2006/0230481 P1 Oct. 12, 2006

Related U.S. Application Data

(60) Provisional application No. 60/669,803, filed on Apr. 7, 2005.

(51) Int. Cl.
*A01H 5/00* (2006.01)

(52) U.S. Cl. ..... Plt./291

(58) Field of Classification Search ..... Plt./291
See application file for complete search history.

(56) References Cited

PUBLICATIONS

2005 Ficor Catalogue listing the *Chrysanthemum* variety 'Calabria Dark Pink'. See, e.g., pp. 3 (photograph), 5 and 13. Catalogue was published Jan. 25, 2005.

2004 Cleangro Brochure listing the *Chrysanthemum* variety 'Calabria Dark Pink'. See photograph at p. 4. Brochure was published Sep. 1, 2003.

2005 Cleangro Brochure listing the *Chrysanthemum* variety 'Calabria Dark Pink'. See photograph at p. 5. Brochure was published Sep. 1, 2004.

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Posh Pink', having an upright growth habit and medium soft pink decorative flowers with a greenish center.

1 Drawing Sheet

Latin name of the genus and species: Botanical classification: *Chrysanthemum morifolium.*

Variety denomination: The new *Chrysanthemum* variety denomination is 'Posh Pink'.

BACKGROUND OF THE INVENTION

The present invention comprises a new and distinct cultivar of *Chrysanthemum* botanically known as *Chrysanthemum morifolium,* and referred to by the cultivar name 'Posh Pink'.

'Posh Pink', identified as 14604-0 originated from a cross made in a controlled breeding program in Chichester, West Sussex, United Kingdom. The female parent of the new variety is an unknown undistributed, unpatented seedling and the male parent is an unknown undistributed, unpatented seedling. The new variety 'Posh Pink' has been asexually reproduced by vegetative cuttings, in Chichester, West Sussex, United Kingdom and the distinguishing characteristics are retained through successive generations of asexual reproduction.

BRIEF SUMMARY OF THE INVENTION

'Posh Pink' is a cut type of *Chrysanthemum* plant variety having a slightly domed capitulum of pink decorative type flowers.

Comparison With The *Chrysanthemum* Variety 'Calabria Dark Pink'

Plants of the new *Chrysanthemum* variety 'Posh Pink' are dissimilar to plants of the unpatented variety 'Calabria Dark Pink' in plant habit and growth rate. In side-by-side comparisons in Chichester, West Sussex, United Kingdom, under commercial practice, plants of the new *Chrysanthemum* variety 'Posh Pink' differed from plants of 'Calabria Dark Pink' in the following characteristics:

1. The new variety 'Posh Pink' produces rose pink medium sized decorative type flowers whereas 'Calabria Dark Pink' produces deep pink larger sized decorative type flowers.
2. Plants of the new variety 'Posh Pink' have smaller and shorter inflorescence than plants of 'Calabria Dark Pink'.
3. Plants of the new variety 'Posh Pink' flower after about 47 Short Days whereas plants of the variety 'Calabria Dark Pink' flower after about 54 Short Days.
4. Plants of the new variety 'Posh Pink' are less vigorous than plants of the variety 'Calabria Dark Pink'.

BRIEF DESCRIPTION OF ILLUSTRATIONS

Typical specimens of the plant and flowers for the new *Chrysanthemum* variety 'Posh Pink' are shown in the accompanying scanned image printed from a photograph. The colors shown are as true as possible within the usual limits of this kind of illustration.

FIG. 1 is a side perspective view of a typical flowering stem of the new variety grown as a cut flower. The plant shown in the illustration is 47 days from the onset of Short Days.

DETAILED BOTANICAL DESCRIPTION

The following description of the new *Chrysanthemum* variety 'Posh Pink' is of plants grown in the soil for 47 Short Days in a greenhouse in Chichester, West Sussex, United Kingdom, in the month of February. The cultivar has not been observed under all possible environmental conditions. The phenotype may vary significantly with variations in the environment such as temperature, length of day and light intensity, without any variance in genotype. The commercial classification of the new variety is a cut flower *Chrysanthemum.*

Plants of the new variety have been grown successfully under temperature conditions averaging about 18° C. at night and about 18° C. to 24° C. during the day under light conditions of about 5,000 to 6,000 foot candles. The plants respond well to the use of growth retardant, such as one B9 treatment at about one gram/liter. To produce a commercial product, the plants may be pinched and with the center bud removed. It has been observed that the shelf life of the new variety is about 18 days with a response time of about 7 weeks. The new variety is suitable for growth in a temperature range of 18° C. to 25° C.

The new variety may be produced as a spray. The following description is with respect to a plant produced as spray *Chrysanthemum.* In the description of this new *Chrysanthemum* variety, color values have been taken from The Royal Horticultural Society Colour Chart (R.H.S.C.C.).

Plant

Plant type: Decorative flower cut *Chrysanthemum.*
Habit: Upright.
Height (cm): 75–100.
Width (cm): 12–15.
Stem:
- *Length* (*cm*).—75–100.
- *Diameter* (*cm*).—0.7–0.9.
- *Texture.*—Smooth, slightly pubescent.
- *Color.*—Near 146B.

Branching characteristics:
Lateral branches:
- *Length* (*cm*).—7–12.
- *Diameter* (*cm*).—0.2–0.3.
- *Texture.*—Smooth, slightly pubescent.

Number of breaks from pinch: 9–12.
Response time: Near 47 days.
Vigor: Medium.
Shelf life: Near 18 days.
Life of blooms: Near 18 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 1 application of 1 gm/liter B9 @ 21 after sticking unrooted cuttings.
The plants were grown for 2 weeks in Long Day conditions (20 hours of light) and then transferred to Short Day conditions (13 hours of dark).
Propagation:
- *Type.*—Vegetative propagation via stem cuttings.
- *Time to rooting.*—12 days with soil temperatures of 22° C.
- *Rooting habit.*—After 7 Long Days, the first roots emerge and form root primordia. In 12 Long Days, a complete root system is developed.

Foliage

Number of leaves per lateral branch: 32–38.
Compound or single: Single.
Arrangement of leaves: Alternate.
- *Shape of leaf.*—Typically 5 lobed.
- *Size of leaf.*—Width (cm): 4–8. Length (cm): 8–14.
- *Leaf apex.*—Mucronate.
- *Base.*—Rounded.
- *Attachment.*—Petioled.
- *Aspect.*—Slightly undulating.
- *Margin.*—Palmately lobed.
- *Surface characteristics.*—Top: Smooth, slightly pubescent. Bottom: Veined, slightly pubescent.

Petiole:
- *Color.*—Near 138A.
- *Length* (*cm*).—2–3.
- *Diameter* (*cm*).—0.2–0.4.
- *Surface.*—Slightly pubescent.

Venation: Net, prominent lateral and mid-veins at underside.
- *Color.*—Upper side: Near 144A. Under side: near 143A.

Color:
- *Mature leaf, upper side.*—Near 137B; under side: Near 138B.
- *Young leaf, upper side.*—Near 143A; under side: Near 138B.

Flower

Flower appearance: Matte.
Flower type: Decorative.
Flower form: Domed.
Flower shape: Round.
Flowering habit: Cylindrical.
Number of blossoms per branch: 7–10.
Typical and observed flowering season: Year Round.
Inflorescence form: Corymbiform.
- *Depth of fully expanded blossoms* (*cm*).—2–3.
- *Diameter of fully expanded blossoms* (*cm*).—5.5–7.5.

Phyllaries:
- *Number.*—15–20.
- *Color.*—Near 137B.
- *Length* (*cm*).—0.4–0.6.
- *Width* (*cm*).—0.15–0.25.
- *Texture/appearance.*—Slightly shiny and slightly pubescent.

Pedicel:
- *Length* (*cm*).—7–12.
- *Diameter* (*cm*).—0.25–0.4.
- *Angle from stem* (*degrees*).—20–25.
- *Color.*—Near 138C.
- *Surface.*—Pubescent.
- *Habit.*—Very slightly curving.
- *Strength.*—Strong.

Ray florets:
- *Form/shape.*—Straight.
- *Texture/appearance.*—Dull, slightly ridged.
- *Number per flower.*—210–220.
- *Length* (*cm*).—4.5–5. Width (cm): 0.5–1.
- *Apex.*—Round.
- *Base.*—Tubular.
- *Margin.*—Entire.
- *Disc florets.*—No disc florets.
- *Diameter of disc* (*cm*).—0.56.

Fragrance: None.

Flower bud (at onset of color):

*Length* (*cm*).—0.7–0.9.

*Diameter* (*cm*).—0.9–1.1.

*Form/shape*.—Globular.

General flower color:

1. *Ray florets, upper side*.—Immature: near 68A. Mature: near 68C. Older/fading: near 68D.
2. *Ray florets, under side*.—Immature: near 68A. Mature: near 68C. Older/Fading: near 68D.
3. *Disc florets*.—No disc florets.
6. *Bud*.—Near 137A.

Flower progression with age: Uniform fading with age.

Other distinguishing characteristics: Green appearance to flower centre: near 140A.

Reproductive Organs

Gynoecium present on ray florets per individual flower: Pistillate.

*Pistil number*.—150–210 observed.

*Stigma color*.—Near 151B.

*Stigma shape*.—Forked.

*Style color*.—Near 151B.

*Style length* (*cm*).—0.1–0.2.

Androecium: Not observed.

Fruit and seeds: None observed.

What is claimed is:

1. A new and distinct variety of *Chrysanthemum* plant, substantially as described and illustrated herein.

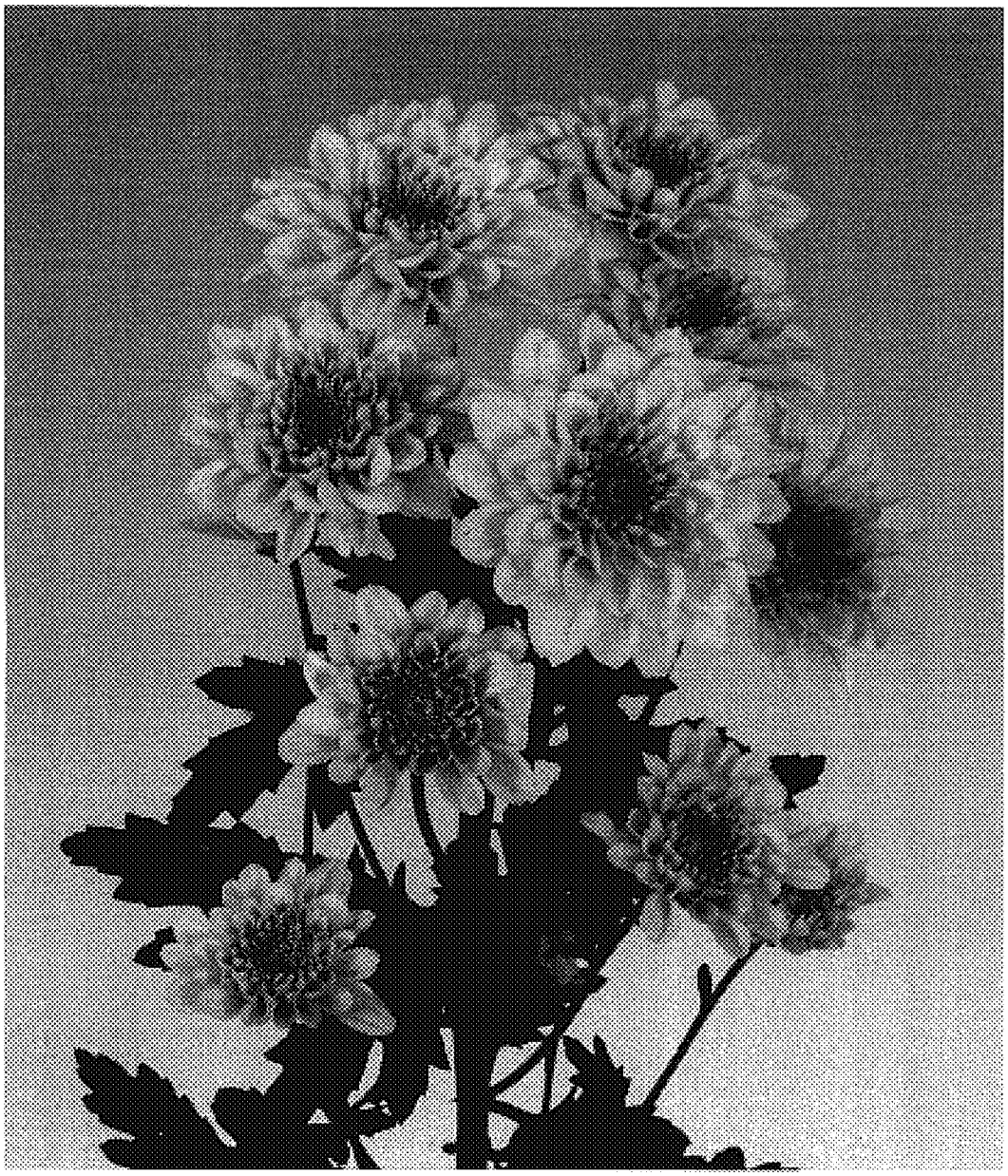

* * * * *